US010526663B2

(12) United States Patent
Baumstummler et al.

(10) Patent No.: US 10,526,663 B2
(45) Date of Patent: Jan. 7, 2020

(54) METHOD OF DETECTING A MICROORGANISM IN A SAMPLE BY A FLUORESCENCE BASED DETECTION METHOD

(71) Applicants: Merck Patent GmbH, Darmstadt (DE); SOMALOGIC, Inc., Boulder, CO (US)

(72) Inventors: Anne Baumstummler, Gertwiller (FR); Frederic Marc-Kreucher, Itterswiller (FR); David Lehmann, Andolsheim (FR); Urs Ochsner, Denver, CO (US); Nebojsa Janjic, Boulder, CO (US)

(73) Assignees: Merck Patent GmbH, Darmstadt (DE); SOMALOGIC, Inc., Boulder, CO (US)

( * ) Notice: Subject to any disclaimer, the term of this patent is extended or adjusted under 35 U.S.C. 154(b) by 0 days.

(21) Appl. No.: 15/119,987

(22) PCT Filed: Feb. 20, 2015

(86) PCT No.: PCT/EP2015/000393
§ 371 (c)(1),
(2) Date: Aug. 18, 2016

(87) PCT Pub. No.: WO2015/124315
PCT Pub. Date: Aug. 27, 2015

(65) Prior Publication Data
US 2017/0051337 A1   Feb. 23, 2017

(30) Foreign Application Priority Data

Feb. 21, 2014 (EP) ..................................... 14290046
Feb. 21, 2014 (EP) ..................................... 14290047

(51) Int. Cl.
*C12Q 1/68* (2018.01)
*G01N 15/14* (2006.01)
*G01N 21/64* (2006.01)
*C12Q 1/689* (2018.01)
*G01N 15/00* (2006.01)

(52) U.S. Cl.
CPC ......... *C12Q 1/689* (2013.01); *G01N 15/1436* (2013.01); *G01N 21/6428* (2013.01); *G01N 2015/0065* (2013.01); *G01N 2021/6439* (2013.01); *G01N 2201/06113* (2013.01)

(58) Field of Classification Search
None
See application file for complete search history.

(56) References Cited

U.S. PATENT DOCUMENTS

| | | |
|---|---|---|
| 7,947,447 B2 | 5/2011 | Zichi et al. |
| 2012/0071639 A1 | 3/2012 | Bruno |
| 2015/0056627 A1 | 2/2015 | Karkkainen et al. |

FOREIGN PATENT DOCUMENTS

| | | |
|---|---|---|
| WO | 2013064818 A1 | 5/2013 |
| WO | 2015126769 A1 | 8/2015 |

OTHER PUBLICATIONS

International Search Report dated Jan. 29, 2015, issued in corresponding PCT/EP2014/075850, 3 pages.
Cao, X. et al., "Combining use of a panel of ssDNA aptamers in the detection of *Staphylococcus aureus*", Nucleic Acids Research, 2009, vol. 37, No. 14, pp. 4621-4628.
Dwivedi, H.P., et al., "Selection of DNA aptamers for caption and detection of *Salmonella typhimurium* using a whole-cell SELEX approach in conjunction with cell sorting", Appl Microbiol Biotechnol, 2013, pp. 3677-3686.
Gold L. et al., "Aptamer-Based Multiplexed Proteomic Technology for Biomarker Discovery", PLOS one, vol. 5 Issue 12, Dec. 2010, e15004, pp. 1-17.
Vaught J. D. et al., "Expanding the Chemistry of DNA for in Vitro Selection", J. Am. Chem. Soc., 2010, 132, pp. 4141-4151.
Ochsner U.A., et al., "Detection of Clostridium difficile toxins A, B and binary toxin with slow off-rate modified aptamers", Diagnostic Microbiology and Infectious Disease 76, 2013, pp. 278-285.
Marraffini L. A. et al., "Sortases and the Art of Anchoring Proteins to the Envelopes of Gram-Positive Bacteria", Microbiology and Molecular Biology Reviews, vol. 70, No. 1, Mar. 2006, pp. 192-221.
McDevitt D. et al., "Characterization of the interaction between the *Staphylococcus aureus* clumping factor (ClfA) and fibrinogen", Eur. J. Biochem, 247, 1997, pp. 416-424.
Eidhin, N. D. et al., "Clumping factor B (ClfB), a new surface-located fibrinogen-binding adhesin of *Staphylococcus aureus*" Molecular Microbiology 1998, 30(2), pp. 245-257.
Roche F. M. et al., "The N-terminal A Domain of Fibronectin-binding Proteins A and B Promotes Adhesion of *Staphylococcus aureus* to Elastin", The Journal of Biological Chemistry, 2004, vol. 279, No. 37, pp. 38433-38440.

(Continued)

*Primary Examiner* — Robert A Zeman
(74) *Attorney, Agent, or Firm* — Millen, White, Zelano & Branigan, PC (57) ABSTRACT

The present invention relates to a method of detecting a microorganism, in particular *Staphylococcus aureus*, in a sample, comprising the steps of a) incubating the sample with a slow off-rate modified aptamer (SOMAmer) comprising a fluorescent label, b) optionally washing the sample, c) analyzing the sample by a fluorescence-based detection method.

The invention further relates to a slow off-rate modified aptamer comprising a fluorescent label, wherein the SOMAmer comprises a nucleotide sequence specific for *Staphylococcus aureus*, its use for detecting *Staphylococcus aureus* cells in a sample, and to a microarray or biosensor and a kit comprising at least one of such SOMAmers comprising a fluorescent label.

6 Claims, 3 Drawing Sheets

Specification includes a Sequence Listing.

(56) References Cited

OTHER PUBLICATIONS

Roche F. M. et al., "Characterization of novel LPXTG-containing proteins of *Staphylococcus aureus* identified from genome sequences", Microbiology 2003, 149, pp. 643-654.

Ythier M. et al, "Proteomic and Transcriptomic Profiling of *Staphylococcus aureus* Surface LPXTG-proteins: Correlation with agr Genotypes and Adherence Phenotypes" Molecular and Cellular Proteomics, 2012, pp. 1123-1139.

Grigg J. C. et al., "Structural biology of heme binding is the *Staphylococcus aureus* lsd system", Journal of inorganic Biochemistry 104, 2010, pp. 341-348.

Mazmania S. K. et al., "Passage of Heme-Iron Across the Envelope of *Staphylococcus aureus*", Science, Feb. 2003, vol. 299, pp. 906-909.

Alvarez-Barrientos A., et al, "Applications of Flow Cytometry to Clinical Microbiology", Clinical Microbiology Reviews, vol. 13, No. 2, 2000, pp. 167-195.

Reynolds D. T. et al., "Application of laser scanning for the rapid and automated detection of bacteria in water samples", Journal of Applied Microbiology, 1999, 86, pp. 785-795.

Vanhee L.M.E. et al., "Detection and quantification of viable airborne bacteria and fungi using solid-phase cytometry", Nature Protocols, vol. 4, No. 2, 2009, pp. 224-231.

Kraemer S. et al., "From SOMAmer-Based Biomarker Discovery to Diagnostic and Clinical Applications: A SOMOmer-Based, Streamlined Mulitiplex Proteomic Assay" PLOS ONE, vol. 6, No. 10, 2011, pp. 1-13.

Hamula C. L. A. et al., "Selection and analytical applications of aptamers binding microbial pathogens", Trac, Trends in Analytical Chemistry, vol. 30, No. 10, 2011, pp. 1587-1597.

Baumstummler A. et al., "Specific capture and detection of *Staphylococcus aureus* with high-affinity modified aptamers to cell surface components", Letters in Applied Microbiology, vol. 59, No. 2, 2014, pp. 422-431.

European Office Action issued in European Patent Application No. 15706159.9, dated Jun. 2, 2017.

METHOD OF DETECTING A MICROORGANISM IN A SAMPLE BY A FLUORESCENCE BASED DETECTION METHOD

The present invention relates to a method of detecting a microorganism, in particular *Staphylococcus aureus*, in a sample, comprising the steps of a) incubating the sample with a slow off-rate modified aptamer (SOMAmer) comprising a fluorescent label, b) optionally washing the sample, c) analyzing the sample by a fluorescence-based detection method.

The invention further relates to a SOMAmer comprising a fluorescent label, wherein the SOMAmer comprises a nucleotide sequence specific for *Staphylococcus aureus*, its use for detecting *Staphylococcus aureus* cells in a sample, and to a microarray or biosensor and a kit comprising at least one of such SOMAmers comprising a fluorescent label.

Monitoring for microbial contamination of food, water, non-sterile products, or the environment is typically based on traditional microbiology methods, such as culture methods. For the detection of a particular micro-organism, one can use selective or differential culture media that respectively allow the growth of only selected micro-organisms or the differentiation of one micro-organism type from another growing on the same media. These methods require several days to give a result because they rely on the ability of micro-organisms to grow to yield visible colonies. Even if they are time-consuming, they remain the standard detection methods.

Over the past two decades, many technologies and detection systems arose in the field of rapid microbiology, such as nucleic acid amplification-based technologies (NAAT) and immunoassays. These alternative technologies reduce the detection time compared to traditional culture-based methods.

NAAT are known to give contamination result in a few hours. However, this technology has several drawbacks, such as the complexity of the protocols which require high technical skills or false positive issues and are still limited by the sample preparation method.

Immunoassays rely on the use of specific monoclonal or polyclonal antibodies to either capture and/or detect the target micro-organism. The efficiency and the success of an immunoassay rely on the quality of the antibodies being used in the test. Due to the way they are produced (in animals or by cell-culture), one drawback of using antibodies is the issue with the batch-to-batch reproducibility.

To overcome certain drawbacks of antibodies and improve assay quality, new affinity binders have been developed, such as aptamers.

Aptamers are synthetic, short DNA or RNA strands that can fold into a variety of structures and can bind specifically, like an antibody, to its target.

DNA aptamers have already been used for the detection of micro-organisms (including *S. aureus*). Moreover, fluorescence-labeled DNA aptamers have also been reported for the detection of whole bacterial cells using fluorescence-based methods:

US 2012/0071639 A1 discloses specific DNA sequences for binding various foodborne and waterborne pathogens and biotoxins.

WO 2013/064818 A1 discloses fluorescence-labeled aptamers for the detection of pathogenic bacteria in a sample.

Cao et al. (2009, Nucleic Acids Res 37, 4621-4628) discloses a panel of ssDNA aptamers specific to *Staphylococcus aureus* obtained by a whole bacterium SELEX procedure. The combination of five of these aptamers resulted in a good effect in the recognition of different *S. aureus* strains.

Dwivedi et al. (2013, Appl Microbiol Biotechnol 97, 3677-3686) describes DNA aptamers specific for *Salmonella enterica* serova Typhimurium and their use for the detection of *Salmonella* by flow cytometry.

Gold et al. (2010, PLoS One 5, e15004) and Vaught et al. (2010, J Am Chem Soc 132, 4141-4151) describe the development of a new aptamer-based reagent called SOMAmer (slow off-rate modified aptamer). SOMAmers are made from single-stranded DNA (ssDNA) that contain pyrimidine residues modified at their 5-prime position with mimics of amino acid side-chains and have quite long (>30 min) dissociation rates. These features lead to better affinity and better kinetic properties of SOMAmers compared to standard RNA or DNA aptamers.

U.S. Pat. No. 7,947,447 B2 discloses improved SELEX methods for producing SOMAmers that are capable of binding to target molecules with slower dissociation rate constants than are obtained using prior SELEX methods.

Ochsner at al. (2013, Diagn Microbiol Infect Dis. 76, 278-285) describes the characterization of SOMAmers specific for *Clostridium difficile* toxins, i.e. microbial proteins.

The use of SOMAmers for the detection of whole bacterial cells has not been described in the state of the art.

The object of the present invention was the provision of suitable reagents for the detection of microorganisms in complex samples.

Surprisingly it was found that highly specific fluorescence-labeled SOMAmers are a very effective tool for the detection of microorganisms in complex samples via fluorescence-based methods.

The present invention therefore relates to a method of detecting a microorganism in a sample, comprising the steps of a) incubating the sample with a slow off-rate modified aptamer (SOMAmer) comprising a fluorescent label, b) optionally washing the sample, c) analyzing the sample by a fluorescence-based detection method.

SOMAmers (slow off-rate modified aptamers) are made from single-stranded DNA (ssDNA) that contain pyrimidine residues modified at their 5-prime position with mimics of amino acid side-chains and have quite long (>30 min) dissociation rates. These features lead to better affinity and better kinetic properties of SOMAmers compared to standard RNA or DNA aptamers (Gold et al., 2010, PLoS One 5, e15004; Vaught et al., 2010, J Am Chem Soc 132, 4141-4151).

As used herein "slow off-rate" refers to the time it takes for an aptamer/target complex to begin to dissociate. This can be expressed as a half life or the point at which 50% of the aptamer/target complex has dissociated. The off-rate or dissociation rate of a SOMAmer, expressed as half-life ($t_{1/2}$) values, can be more than 30 min, more than 60 min, more than 90 min or more than 120 min. The dissociation time can be measured by dynamic systems monitoring the association and dissociation of complexes well known in the art, e.g. Surface Plasmon Resonance.

SOMAmer reagents can be generated to cell surface-associated proteins of microorganisms via SELEX methods with multiple modified DNA libraries using native or purified recombinant proteins. Suitable SELEX methods for generating such SOMAmers are disclosed in U.S. Pat. No.

7,947,447 B2, which is incorporated by reference to the disclosure of the present patent application.

Conventional chemical, microbiological and molecular biological methods necessary to practice the invention are known to a person skilled in the art and can also be found in standard literature.

According to the present invention, the term microorganism relates to bacteria, yeast or fungi. In a preferred embodiment the microorganism is a bacterium, preferably a pathogenic bacterium.

It can, for example, be selected from the group consisting of *Salmonella* spp. (such as *Salmonella typhimurium*, *Salmonella enteritidis*), *Escherichia coli*, *Listeria* spp, *Listeria monocytogenes*, *Staphylococcus aureus*, *Pseudomonas*, *Campylobacter*, *Shigella*, *Streptococcus*, *Mycobacterium*, *Burkholderia*, *Legionella*, *Yersinia*, *Clostridium*, *Corynebacterium* and *Vibrio*.

In a preferred embodiment of the present invention the microorganism is *Staphylococcus aureus*.

Examples for surface-associated proteins of *Staphylococcus aureus*, to which SOMAmers can for example be prepared, include SpA, ClfA, ClfB, FnbA, FnbB, SasD, IsdA, IsdB, IsdC, and IsdH. All of these proteins are attached to the cell-wall via sortase-mediated cleavage between the threonine and the glycine of the LPXTG sortase motif and become amide-linked to the pentaglycine cross-bridge of peptidoglycan (Marraffini et al., 2006, *Microbiol Mol Biol Rev* 70: 192-221). *S. aureus* protein A (SpA) is present on the bacterial surface as well as secreted into the extracellular milieu. ClfA and ClfB are structurally related fibrinogen-binding proteins (McDevitt et al., 1997, *Eur J Biochem* 247: 416-424; Ni Eidhin et al., 1998, *Mol Microbiol* 30: 245-257). ClfB is one of the key factors responsible for adherence to desquamated epithelial cells of the anterior nares, and is typically produced during early exponential phase of growth (Ni Eidhin et al., 1998, see above). FnbA and FnbB adhere to components of the extracellular matrix, both fibronectin and elastin, and are important for colonization of host tissues during infection (Roche et al., 2004, *J Biol Chem* 279: 38433-38440). SasD is a putative adhesion protein with unknown physiological role (Roche et al., 2003, *Microbiology* 149: 643-654; Ythier et al., 2012, Mol Cell Proteomics 11: 1123-1139). Four of the proteins belong to the iron-responsive surface determinant (Isd) system that is induced in *S. aureus* under iron-limiting conditions and is important for capture of heme from hemoglobin (IsdB, IsdH) and its transport (IsdA, IsdC) across the cell wall (Grigg et al., 2010, *J Inorg Biochem* 104: 341-348; Mazmanian et al., 2003, Science 299: 906-909).

Typically, the sample to be analyzed is a complex sample, such as a clinical sample, a food or feed sample, a beverage sample, a pharmaceutical sample (including water for injection), a personal care and/or cosmetic sample. The sample may be a raw ingredient, a finished product or may be taken from the environment of manufacture or storage. Preferably, the sample is a clinical sample, a food sample, a pharmaceutical sample and/or a personal care product.

"Complex sample" means a sample which comprises more than one component. For example when it is a food or feed—it may be meat or a meat product (e.g. raw or cooked meat product), a dairy product or a composition used in the production of a dairy product, such as cheese or yoghurt, a vegetable based food product, a ready to eat food or a food ingredient, a salad product, an infant formula. In one embodiment the sample may be a personal care or cosmetic product such as an eye care product, such as contact lens solution. If the sample is a beverage, it may be for example beer or a sample taken during the brewing of beer, drinking water. Pharmaceutical samples cover pharmaceuticals for humans as well as for animals (i.e. veterinary applications). A clinical sample may for example be a body fluid, in particular blood, plasma or serum or a tissue sample.

Exemplary samples include, but are not limited to, food (e.g. milk of cows, ewes, nanny goats, mares, donkeys, camels, yak, water buffalo and reindeer, milk products, meat of beef, goat, lamb, mutton, pork, frog legs, veal, rodents, horse, kangaroo, poultry, including chicken, turkey, duck, goose, pigeon or dove, ostrich, emu, seafood, including finfish such as salmon and tilapia, and shellfish such as molluscs and crustaceans and snails, meat products, plant products, seeds, cereals from grasses, including maize, wheat, rice, barley, sorghum, and millet, cereals from non-grasses, including buckwheat, amaranth, and quinoa, legumes, including beans, peanuts, peas, and lentils, nuts, including almonds, walnuts, and pine nuts, oilseeds, including sunflower, rape and sesame, vegetables like root vegetables, including potatoes, cassava and turnips, leaf vegetables, including amaranth, spinach and kale, sea vegetables, including dulse, kombu, and dabberlocks, stem vegetables, including bamboo shoots, nopales, and asparagus, inflorescence vegetables, including globe artichokes, broccoli, and daylilies, and fruit vegetables, including pumpkin, okra and eggplant, fruits, herbs and spices, whole blood, urine, sputum, saliva, amniotic fluid, plasma, serum, pulmonary lavage and tissues, including but not limited to, liver, spleen, kidney, lung, intestine, brain, heart, muscle, pancreas and the like. The skilled artisan will appreciate that lysates, extracts or (homogenized) material obtained from any of the above exemplary samples or mixtures of said exemplary samples or compositions comprising one or more of said exemplary samples are also samples within the scope of the invention.

In one embodiment of the present invention, the SOMAmer comprises a nucleotide sequence specific for *Staphylococcus aureus*.

The term "nucleotide sequence" as used herein refers to an oligonucleotide sequence or polynucleotide sequence, and variant, homologues, fragments and derivatives thereof (such as portions thereof). The nucleotide sequence may be of synthetic or recombinant origin, which may be single-stranded whether representing the sense or anti-sense strand.

The term "nucleotide sequence" in relation to the present invention includes synthetic DNA and RNA. Preferably the nucleotide sequence of the SOMAmer according to the present invention could be synthesised, in whole or in part, using chemical methods well known in the art.

The term "specific" as used herein means that the SOMAmer is selectively reactive with *Staphylococcus aureus* cells compared with other microorganisms.

The SOMAmers according to the present invention may be used in a fashion analogous to antibodies. Like antibodies the SOMAmers provide target binding specificity.

In one aspect of the present invention, the SOMAmer comprises a nucleotide sequence selected from the group consisting of SEQ ID NO:15 and SEQ ID NO:16 or a fragment thereof or a sequence which is at least 80% identical therewith, or a sequence which hybridizes under stringent conditions therewith.

Preferably, the SOMAmer comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12 or a fragment thereof or a sequence which is at least 80% identical therewith, or a sequence which hybridizes under stringent conditions therewith.

More preferably, the SOMAmer comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12.

In a very preferred embodiment of the present invention, the SOMAmer comprises a nucleotide sequence according to SEQ ID NO:1 or SEQ ID NO:3.

The term "fragment" as used herein means a portion of the aptamer sequence taught herein which has the same or better affinity, specificity or functional activity for the target of interest compared with the full sequence. The fragment may be comprised of about 35 nucleotides (e.g. 33-37 nucleotides). The fragment preferably has a secondary structure similar to that of the original full length aptamer over the region represented by the fragment.

The present invention also encompasses the use of sequences having a at least 80% of sequence identity with the nucleic acid sequence(s) of the present invention. In the present context, a similar sequence is taken to include a nucleotide sequence which may be at least 80%, preferably at least 90% identical, more preferably at least 95 or 98% identical to the subject sequence. Typically, the similar sequences will comprise the same or similar secondary structure as the subject SOMAmer.

In one embodiment, a similar sequence is taken to include a nucleotide sequence which has one or several additions, deletions and/or substitutions compared with the subject sequence.

Sequence identity comparisons can be conducted by eye, or more usually, with the aid of readily available sequence comparison programs. These commercially available computer programs can calculate % identity between two or more sequences.

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing". The hybridization takes place under stringent conditions (e.g. 50° C. and 0.2×SSC {1×SSC=0.15 M NaCl, 0.015 M $Na_3$ citrate pH 7.0}).

According to the present invention the SOMAmers comprise a fluorescent label.

The label may be attached to either the 5' or 3' end of the SOMAmer. In a preferred embodiment the label is attached to the 5'-end of the SOMAmer. The skilled person is well aware of techniques for attaching fluorescent labels to nucleic acid strands. Any one of these methods may be utilized in the present invention to attach a fluorescent label to the SOMAmers, e.g. as described by Schubert et al, 1990, *Nucleic Acids Research* 18, 3427. In principle, the fluorescent label can be attached during or after the oligonucleotide synthesis.

The fluorescent label may be attached directly or indirectly to the SOMAmer. For indirect attachment any mechanism known to the person skilled in the art can be used, such as using biotin and streptavidin or Digoxigenin (DIG) and Antidigoxigenin.

The suitable fluorescent label is selected by the person skilled in the art depending on different parameters, such as the size of the label and/or the optical properties, such as the colour, the fluorescence excitation wavelengths, the fluorescence emission wavelengths and intensity. A large variety of fluorescent labels is commercially available. Examples for suitable fluorescent labels are fluorescein dyes (such as fluorescein, 6-FAM (6-carboxyfluroescein), JOE, TET, HEX), rhodamine dyes (such as 5'-Tamra, ROX, TRITC, X-Rhodamine, Lissamine Rhodamine B), cyanine dyes (such as Cy2, Cy3, Cy3B, Cy3.5, Cy5, Cy5.5, Cy7, IRD700, IRD800, Allophycocyanin (APC)), Peridinin chlorophyll (PerCP), R-Phycoerythrin (R-PE), coumarine dyes (such as hydroxycoumarine, aminocoumarine, methoxycoumarine) and quantum dots. Further examples are Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, Alexa Fluor® 790, DyLight 350, DyLight 408, DyLight 488, DyLight 549, DyLight 594, DyLight 633, DyLight 649, DyLight 680, DyLight 759, DyLight 800, eFluor® 660, Cascade Blue, Pacific Blue, Pacific Orange, Lucifer Yellow, NBD, Red 613, TruRed, FluorX, BODIPY-FL, Texas Red. Preferably, fluorescein is used.

The method according to the present invention involves in step a) the incubation of the sample with a slow off-rate modified aptamer (SOMAmer) comprising a fluorescent label. This means that the SOMAmers comprising a fluorescent label are admixed with the sample and incubated for a time period.

Typically, the sample is directly inoculated into a buffer or a growth medium (optional incubation) before further analysis by fluorescence-based detection method using the SOMAmers. If the sample is a solid sample, it may be necessary to perform stomaching after or during the addition of the buffer or growth medium. In a further alternative embodiment, the solid sample is rinsed with a fluid which is then collected for further optional incubation in a growth medium and further analysis with the SOMAmers.

Alternatively, the SOMAmers are mixed with a suitable buffer or with a growth medium which is then mixed with the sample. If the sample is a solid sample, it may be necessary to perform stomaching after or during the addition of the buffer/growth medium comprising the SOMAmers.

A suitable buffer can be selected by a person skilled in the art. It typically has a pH value greater than 5 and lower than 9, preferably greater than 6 and lower than 8, more preferably between 6.5 and 7.5. The buffer which may be used in the method of the present invention is preferably selected from the group of phosphate buffer, phosphate buffered saline buffer (PBS), 2-amino-2-hydroxymethyl-1, 3-propanediol (TRIS) buffer, TRIS buffered saline buffer (TBS) and TRIS/EDTA (TE). In one embodiment of the present invention the buffer further comprises $MgCl_2$. The $MgCl_2$—if present—is typically present in concentrations between 0.005 and 3 M, preferably between 0.01 and 1 M, more preferably between 0.01 and 0.5 M, e.g. 25 mM.

Typically, approximately 0.07 μmol/L of SOMAmers would be sufficient for the detection of $10^7$ cells of target microorganisms in a sample. In a preferred embodiment a SOMAmer concentration of 0.01 to 10 μmol/l buffer is used.

The incubation is typically performed at temperatures between 16° C. and 30° C., preferably between 18° C. and 28° C., more preferably at room temperature.

Typically, the time period for incubation is between 1 and 60 min, preferably between 5 and 30 minutes.

The concentration of SOMAmers used in accordance with the present invention may be determined by a person skilled in the art.

Optionally the method according to the present invention may involve a step of washing the sample. During this step any unbound SOMAmer may be washed off before detecting the presence of bound SOMAmer.

Typically, washing means that the sample is centrifuged and the pellet is resuspended in buffer. The washing step can be done once or repeated several times, e.g. twice, 3 times or 4 times.

In step c) according to the present invention the sample is analyzed by a fluorescence-based detection method. The fluorescence-based detection method is preferably selected from the group consisting of flow cytometry, solid-phase cytometry, fluorescence-based analytical methods, and fluorescence imaging system (such as fluorescence microscopy).

Flow cytometry is an analytical method that allows the measurement of light scattered and fluorescence emission produced by illuminated single cells. Typically, the cells or particles to be analyzed are suspended in a liquid and pass individually through a laser beam. The scattered light (related to the particle's size and complexity) and fluorescence emissions (due to fluorescence labeling of the target particle/cell) of each particle are collected by detectors and sent to a computer. Since each particle or cell is interrogated separately, the results represent cumulative individual cytometric characteristics (Álvarez-Barrientos et al. 2000, Clin Microbiol Rev, 13(2): 167-195).

The sample that may contain the target analyte is mixed with a reagent specific to the target analyte (e.g. the SOMAmers according to the present invention) labeled with a suitable fluorescent molecule. After applying proper binding conditions and optional washing steps, the labeled sample is then processed by the flow cytometer: cells pass individually through the laser beam and the resulting scattered light and fluorescence signal are analyzed to collect information related to the target analyte (e.g. cells).

A fluorescence imaging system provides an image of observed objects (e.g. single cells, micro-colonies) which is formed using light emitted from fluorescent phenomenon (Barrett and Myers 2003, Foundations of Image Science. In Wiley Series in pure and Applied Optics ed. Saleh B. E. A. USA, New Jersey, Hoboken: John Wiley & Sons, Inc). Fluorescence microscopy is an example of fluorescence imaging system in which the imaged features are small and obtained through an optical magnification.

The sample that may contain the target analyte is mixed with a reagent specific to the target analyte (e.g. SOMAmers) labeled with a suitable fluorescent molecule. After applying proper binding conditions and optional washing steps, the labeled sample is placed under the microscope objective. The microscope parameters are set to match the fluorescent label properties.

Solid-phase cytometry is a method for detecting single particles/cells on a solid surface. Typically the solid phase cytometry is realized on a membrane. The image-based quantification system will provide the amount, size and shape of any selected markers in conjunction with their localization on the membrane.

The sample, that may contain the target analyte, is filtered over a black membrane filter (e.g. polyester or polycarbonate) with an appropriate pore size (i.e. 0.4 µm for bacteria). Then, the retained cells are labeled with a reagent specific to the target analyte (e.g. SOMAmers) labeled with a suitable fluorescent molecule. The filter is subsequently scanned with a laser which allows fluorescent events (e.g. labeled micro-organisms) on the membrane to be detected by a series of detection units. This permits the detection and enumeration of the target analyte on a membrane (Reynolds and Fricker 1999, *J Appl Microbiol* 86, 785-795; Vanhee et al. 2009, *Nat Protoc* 4, 224-231).

Fluorescence-based analytical method is a method measuring an overall amount of fluorescence signal that is used to detect and/or measure the amount of a target analyte which has been labeled with a suitable fluorescent tag (Skoog et al. 2007, Principles of Instrumental Analysis, Sixth edition, USA, California, Belmont: Brooks/Cole). This type of method can be implemented in a wide range of supports (e.g. microplate, tube, microtube, microfluidic device).

The sample that may contain the target analyte is mixed with a reagent specific to the target analyte (e.g. SOMAmers) labeled with a suitable fluorescent molecule. After applying proper binding conditions and optional washing steps, the container with the labeled sample (e.g. microplate, tube) is exposed to a specific wavelength meant to properly excite the fluorescent dye. The fluorescence emission, occurring as a consequence of the binding between the target analyte and the fluorescent reagent, is collected by a proper light sensor. This amount of fluorescence is quantified by the sensor and processed in correlation with reference data to provide a measure of the analyte.

Any fluorescent molecule can be used with any fluorescence-based detection method. The key requirement is the availability for a given detection method of a suitable excitation source and a suitable fluorescence detector for the chosen fluorescent molecule.

Examples of wavelengths combinations used for fluorescence detection (suitable fluorescent labels):

Excitation: 488 nm (Blue laser)+Emission: 530 nm (fluorescein, Alexa Fluor® 488), 585 nm (R-Phycoerythrin—R-PE) and >670 nm (Peridinin chlorophyll—PerCP)

Excitation: 532-561 nm (Green and Yellow/Green Laser)+Emission: 560 (Alexa Fluor® 532), 585 (R-PE—R-Phycoerythrin)

Excitation: 635 nm (Red laser)+Emission: 660 nm (Allophycocyanin—APC/Cyanine 5—Cy5/eFluor® 660/Alexa Fluor® 647)

The method according to the present invention provides several advantages over the use of antibodies:
Exceptional thermostability in solution
Lower molecular weight
Higher multiplexing capabilities
Chemical stability to heat, drying and solvents,
Reversible renaturation
Ease of reagent manufacturing
Consistent lot-to-lot performance
Lower cost.

The invention further relates to a slow off-rate modified aptamer (SOMAmer) comprising a fluorescent label, wherein the SOMAmer comprises a nucleotide sequence specific for *Staphylococcus aureus*.

The SOMAmer, the fluorescent label, as well as their preferred embodiments are defined as described above.

Therefore, in another aspect, the present invention relates to a SOMAmer comprising a fluorescent label, characterized in that the SOMAmer comprises a nucleotide sequence selected from the group consisting of SEQ ID NO:15 and SEQ ID NO:16 or a fragment thereof or a sequence which is at least 80% identical therewith, or a sequence which hybridizes under stringent conditions therewith.

In another aspect, the invention relates to a SOMAmer comprising a fluorescent label, characterized in that the SOMAmer comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12 or a fragment thereof or a sequence which is at least 80% identical therewith, or a sequence which hybridizes under stringent conditions therewith.

In a further aspect, the present invention relates to a SOMAmer comprising a fluorescent label, characterized in that the SOMAmer comprises the nucleotide sequence according to SEQ ID NO:1 or SEQ ID NO:3.

In a further embodiment, the present invention relates to the use of a SOMAmer comprising a fluorescent label as defined above for detecting *Staphylococcus aureus* cells in a sample.

The SOMAmers according to the present invention may be immobilized on (e.g. bound or adhered to) a substrate or carrier, e.g. a microcarrier.

The invention also relates to a microarray or biosensor comprising at least one of the SOMAmers comprising a fluorescent label as defined above.

A biosensor is an analytical device for the detection of a target analyte, which converts a biological response into an electrical signal. Biosensor applications use biological recognition elements such as enzymes, antibodies and nucleic acids, to detect the target molecule. A typical biosensor contains three components: a biological sensing element that can recognise or bind the analyte, a transducing element which converts the detection event into a measurable signal, and a display that transforms the signal into a digital format. The sensing element primarily defines the selectivity and sensitivity of the biosensor. The detection of the analytes is usually based on sensing the analytes with either an electrical or optical readout. The SOMAmers comprising a fluorescent label according to the present invention can be used as biological elements in the biosensor application.

The present invention relates in a further embodiment to a kit comprising at least one SOMAmer comprising a fluorescent label as defined above.

The kit according to the present invention may be a rapid detection test kit. The kit may for example comprise i) at least one (such as 2, 3 or 4) SOMAmer comprising a fluorescent label according to the present invention and ii) instructions on how to use the SOMAmers.

BRIEF DESCRIPTION OF DRAWINGS

(a) Representation of the mean fluorescence intensities (columns) and the percentages of stained cells (line) obtained at different SOMAmers concentrations (n=3). Grey columns: mean fluorescence intensity with 4520-8 (SEQ ID NO:3), black columns: mean fluorescence intensity with 4531-56 (SEQ ID NO:1). Black line: percentages of stained cells with either 4520-8 (SEQ ID NO:3) or 4531-56 (SEQ ID NO:1) (identical data).

(b) Example of flow cytometry results obtained with 4531-56 (SEQ ID NO:1) SpA SOMAmers. Black area: unstained cell population; cell population stained with 0.07 µmol l$^{-1}$ (light grey), 0.7 µmol l$^{-1}$ (dark grey) and 7 µmol l$^{-1}$ (solid black line). M1 and M2 intervals are set up to include in M1 the fluorescence signal of the control unstained cells (autofluorescence). Therefore, cell populations located in the M2 interval are considered as stained.

EXAMPLES

Example 1: Purification of *S. Aureus* Targets

Relevant portions of the genes encoding the desired targets or target domains are PCR-amplified from *S. aureus* NRS384 (USA300) genomic DNA with primers shown in Table 1 and cloned into pCR-Script SK+ (Stratgene). The clfA genes are transferred as BamHI-SacI cassettes into the expression vector pET-51 b (EMD-Novagen) that harbors an aminoterminal Strep-tag and a carboxyterminal His$_{10}$-tag. The plasmids are sequenced to verify the gene identity and proper gene fusion of the cloned DNA fragment with the vector-encoded sequences for the His-tag and Strep tag.

TABLE 1

| Amplification and cloning of genes encoding *S. aureus* cell surface proteins | | | | |
|---|---|---|---|---|
| Target | Name | RE site | PCR primers (forward and reverse, with restriction sites underlined) 5' Sequence | Recombinant Protein aa range    Size (kDa) |
| ClfA | clfA-3 | BamHI | C<u>GGATCC</u>AGTAGCTGCAGATGCACC | 221-550    45 |
|  | clfA-4 | SacI | C<u>GAGCTC</u>GCTCATCAGGTTGTTCAGG |  |

The recombinant proteins are over-expressed in *E. coli* BL21(DE3) or in BL21(DE3)/pLysE (EMD/Novagen). Conditions for optimal expression of soluble proteins are optimized with respect to growth temperature (25-37° C.) and induction time (4-15 h). Cells from 0.1-0.8 L cultures are lysed with 10 mL BugBuster/Benzonase reagent (EMD Millipore). The recombinant, His$_{10}$/Strep-tagged proteins are purified from the soluble fraction via sequential affinity chromatography on Ni-NTA agarose and Strep•Tactin® Superflow™ agarose (EMD Millipore). Native staphylococcal protein A is purchased from VWR and is biotinylated with NHS-PEG4-biotin (Pierce Biotechnology). Protein concentrations are determined using the Quick Start Bradford Protein Assay Kit (BioRad).

Example 2: Selection of SOMAmers

Separate libraries with 5-benzylaminocarbonyl-dU (BndU), 5-naphthylmethylaminocarbonyl-dU (NapdU), and 5-tryptaminocarbonyl-dU (TrpdU) are used for SELEX with the S. aureus proteins. Each selection starts from 1 nmol ($10^{14}$-$10^{15}$) sequences containing 40 consecutive randomized positions flanked by fixed sequences required for PCR amplification. SELEX is performed essentially as described (Gold et al. 2010, *PLoS One* 5: e15004; Ochsner et al. 2013, *Diagn Microbiol Infect Dis.*; Vaught et al. 2010, *J Am Chem Soc* 132: 4141-4151). Buffer SB18T is used through-out SELEX and subsequent binding assays, consisting of 40 mM HEPES pH 7.5, 0.1 M NaCl, 5 mM KCl, 5 mM $MgCl_2$, and 0.05% Tween-20. Eight rounds of selection are carried out, and, beginning with round 2, a kinetic challenge with 10 mM dextran sulfate is performed to favor slow off-rates. Partitioning of the SOMAmer-target complexes is achieved with paramagnetic Talon Dynabeads® Talon® (Invitrogen) that bind the $His_{10}$-tag on the recombinant proteins, or with MyOne Streptavidin C1 beads (Life Technologies) for the biotinylated SpA. Selected sequences are eluted from the bead-bound targets with 80 μl 40 mM NaOH, neutralized with 20 μl 160 mM HCl, and PCR-amplified using KOD EX DNA polymerase (Invitrogen-Life Technologies). Modified DNA for the next round is prepared with KOD EX DNA polymerase via primer extension from the antisense strand of the PCR products and purified as described (Gold et al., 2010).

DNA reassociation kinetic analysis ($C_0t$) of selected DNA from rounds 3 through 8 is used for the assessment of sequence convergence during the later rounds, indicating increased abundance of some sequences or sequence families. SOMAmer pools that demonstrate good affinity ($K_d$≤10 nM) in solution binding radioassays (see below) are cloned and the sequences of 48 clones per pool are determined. Individual SOMAmers are chosen based on sequence patterns and diversity and prepared enzymatically for further characterization.

Synthetic SOMAmers are prepared as 48-50-mers at 1 μmol scale via standard phosphoramidite chemistry and HPLC purified. They contain a 5'biotin-dA or 5'fluorescein-biotin-dA, and an inverted dT nucleotide at the 3' end (3'idT) for added stability to 3' to 5' exonucleases.

Example 3: SOMAmers Equilibrium and Whole Cell Radiolabel Binding Assays

SOMAmers are properly folded via heating for 5 min at 95° C., followed by cooling to room temperature over a 10-15 min period, prior to binding assays.

Affinities ($K_d$'s) are determined in equilibrium solution binding assays of radiolabeled SOMAmers (10-20 pM) with serially diluted proteins (0.001-100 nM) and Zorbax PSM-300A (Agilent Technologies) resin for partitioning onto filter plates as described (Gold et al. 2010).

Prior to cloning, the SOMAmers pools are also tested for specific binding to S. aureus, using S. epidermidis, S. hemolyticus, S. pyogenes, E. faecalis, E. coli, and P. aeruginosa as controls in 2 h equilibrium binding assays. Cell densities range from $10^5$-$10^8$ CFU/mL, and 0.1 mM dextran sulfate and 0.35 M NaCl is added to the binding buffer to reduce non-specific background. In addition, individual nucleic acid aptamers are screened for binding to eight different S. aureus strains belonging to different lineages, including NRS382, NRS383, NRS384, NRS123, NRS385, NRS386, NRS103 (NARSA), and ATCC 29213 (ATCC).

Results:

Pool affinity assays confirm the successful selection of SOMAmers for a total of 22 pools obtained with BndU, NapdU, or TrpU modified ssDNA, with pool affinities in the range of 0.13-8.90 nM. Specific binding to S. aureus cells, but no binding to S. epidermidis, S. hemolyticus, S. pyogenes, E. faecalis, E. coli, or P. aeruginosa is observed.

Alignment of sequences determined for 48 clones from each pool show multi-copy clones and families that share common sequence patterns. Representative clones are screened in affinity assays, and the $K_{da}$'s of the best SOMAmers are in the range of 0.03-2.17 nM (Table 2).

TABLE 2

SOMAmer reagents for S. aureus cell surface proteins, with affinity ($K_d$) shown for the original full-length sequences obtained in SELEX.

| | SOMAmer characterization | | |
|---|---|---|---|
| Target | Seq no | Modified | $K_d$ (nM) |
| SPA | 4520-8 (SEQ ID NO: 3) | NapdU | 0.22 |
| SPA | 4531-56 (SEQ ID NO: 1) | TrpdU | 0.03 |
| ClfA | 4503-73 (SEQ ID NO: 12) | BndU | 0.79 |

SOMAmers binding affinities to purified S. aureus proteins correlate well with the observed binding to whole bacteria. One SpA-NapdU clone (4520-8; SEQ ID NO:3) and one of tSpA-TrpdU clone (4531-56; SEQ ID NO:1) are able to bind whole cells of all S. aureus strains tested, with a detection limit of ~$10^4$ cells per well ($10^5$-$10^6$ cells/mL) in a radiolabel filter binding assay. Binding to S. epidermidis or S. hemolyticus cells is not observed, indicating good specificity of these SOMAmers. Similar binding characteristics are observed for the ClfA SOMAmers.

The sequences of the SOMAmers are listed in Table 3.

TABLE 3

Sequences of SOMAmers:

| Target | Seq no | SEQ ID | Sequence |
|---|---|---|---|
| SpA | 4531-56 | SEQ ID NO: 1 | GCTCGAGTTAATTCGGGATCGGGCTCCGGCTTTTCGAAT |
| SpA | 4520-3 | SEQ ID NO: 2 | CCGGCTTCGGGTACCTATTATCGGTTTAGCCCAGTCATAA |
| SpA | 4520-8 | SEQ ID NO: 3 | TCGGCTTCGGGTACCTATTATCGGTTTTAGCCCAGTCAGAA |

TABLE 3-continued

Sequences of SOMAmers:

| Target | Seq no | SEQ ID | Sequence |
|---|---|---|---|
| SpA | 4520-20 | SEQ ID NO: 4 | GCGGCTTCGGGTACCTATTATCGGTTTAGCCCAGTCAAAA |
| SpA | 4520-23 | SEQ ID NO: 5 | GTGGCTTCGGGTACCTATTATCGGTTTAGCCCAGTCAGAA |
| SpA | 4520-27 | SEQ ID NO: 6 | GCGGCTTCGGGTACCTATTATCGGTTTAGCCCTGTCAGGA |
| SpA | 4520-30 | SEQ ID NO: 7 | GTGATCGAGCGGCTTCGGGTACCTATTATTGGTTTAGCCCAGTCAGAA |
| SpA | 4520-42 | SEQ ID NO: 8 | TCGGCTTCGGGTACCTATTATCGGTTTAGCCCAGTCTGAA |
| SpA | 4520-44 | SEQ ID NO: 9 | ACGGCTTCGGGTACCTATTATCGGTTTAGCCA-GTCAGAA |
| ClfA | 4503-66 | SEQ ID NO: 10 | ATCTGGTTCAAAGTGACGATTGGGCATCTGGTTTTTAAGT |
| ClfA | 4503-68 | SEQ ID NO: 11 | ATCTGGTTCTAAGTTACTTGGCGTAATCTGGTTTTTAAGA |
| ClfA | 4503-73 | SEQ ID NO: 12 | ATCTGGTTCAAAGTGGCGATTGGGCATCTGGTTTTTAAGT |

The "T" nucleotide for the sequences provided in Table 3 are C-5 modified pyrimidines. More specifically, the "T" nucleotide for the SOMAmers that target the SpA protein are NapdUTP (or NapdU) nucleotides, and the "T" nucleotide for the SOMAmers that target the ClfA protein are BndUTP (or BndU) nucleotide.

Further, The motif (4520) for the aptamer sequence that binds the SpA protein is represented by the following sequence: GGCWWCGGGWACCWAWWAWNGG-WWWAGCC(N),GWC (SEQ ID NO: 15), wherein the "W" in the sequence represents a position that may be occupied by a C-5 modified pyrimidine, and "N" represents a position that may be occupied by any unmodified or modified nucleotide, and n is from 0 to 2 (or 0, 1 or 2). Preferably, the C-5 modified pyrimidine is a NapdU or a BndU. More preferably, the C-5 modified pyrimidine is a NapdU.

The motif (4503) for the aptamer sequence that binds the ClfA protein is represented by the following sequence: AWCWGGWC(N),AWCWGGWWWWWAAG (SEQ ID NO: 16), wherein the "W" in the sequence represents a position that may be occupied by a C-5 modified pyrimidine, and "N" represents a position that may be occupied by any unmodified or modified nucleotide. Further, n may be a number from 1 to 30 (or 1, 2, 3, 4, 5, 6, 7, 8, 9, 10, 11, 12, 13, 14, 15, 16, 17, 18, 19, 20, 21, 22, 23, 24, 25, 26, 27, 28, 29 or), or from 2 to 20 (or 2, 3, 4, 5, 6, 7, 8, 9, 10, 11, 12, 13, 14, 15, 16, 17, 18, 19 or 20), or from 5 to 18 (or 5, 6, 7, 8, 9, 10, 11, 12, 13, 14, 15, 16, 17 or 18), or from 10 to 16 (or 10, 11, 12, 13, 14, 15 or 16). Preferably, n is 16. Preferably, the C-5 modified pyrimidine is a NapdU or a BndU. More preferably, the C-5 modified pyrimidine is a BndU.

Example 4: Detection of *Staphylococcus Aureus* Cells by Flow Cytometry

SOMAmers to Protein A (SpA) are synthesized as described above as 48-mers containing a 5'ABflT (biotin and fluorescein), for use in flow cytometry experiments. Activity is confirmed for 4520-8 (SEQ ID NO:3) ($K_d$=0.17 nM) and 4531-56 (SEQ ID NO:1) ($K_d$=0.09 nM).

Trypcase Soy Broth (TSB; bioMérieux, Craponne, France) is inoculated with a frozen-preserved culture of *Staphylococcus aureus* DSM 1104 (or ATCC 25923) and incubated overnight at 32.5° C. with shaking. Overnight culture is then subcultured in fresh TSB at 32.5° C. with shaking until the working culture reaches an OD600 of 0.8 (approximately $10^8$ bacteria $ml^{-1}$) and divided into aliquots of approximately $10^7$ cells per tube. Bacteria are harvested by centrifugation at 10 000 g for 2 min. Pellets are resuspended in 100 µl of PBS/25 mmol $l^{-1}$ $MgCl_2$ containing the SOMAmers in a range of concentrations (0.07-7 µmol $l^{-1}$). After incubation at room temperature for 5, 15 or 30 min, the bacteria are centrifuged at 10 000 g for 2 min and the pellets are resuspended with PBS/25 mmol $l^{-1}$ $MgCl_2$. This washing step is repeated twice. Controls of unstained bacteria are included by following the same protocol without adding the SOMAmers. Unstained and stained bacteria are then analyzed by flow cytometry. All experiments are performed with a FACSCalibur™ flow cytometer (Becton Dickinson Biosciences; Le Pont de Claix, France) equipped with an air-cooled 15 mW argon-ion laser emitting at 488 nm. The green fluorescence is collected in the FL1 channel (530±30 nm) as logarithmic signal. The mean fluorescence intensity and the percentage of fluorescent cells (n=10 000 in the defined gate) occurring as a consequence of SOMAmers binding are determined in these assays. Data from the FACSCalibur™ are analyzed using the BD CellQuest™ software (Becton Dickinson Biosciences).

Results:

Fluorescence-labeled SpA SOMAmers 4520-8 (SEQ ID NO:3) and 4531-56 (SEQ ID NO:1) are used to assess their efficiency for the detection of *S. aureus* by flow cytometry. Both SOMAmers perform well in staining whole *S. aureus* cells.

Figure 1:
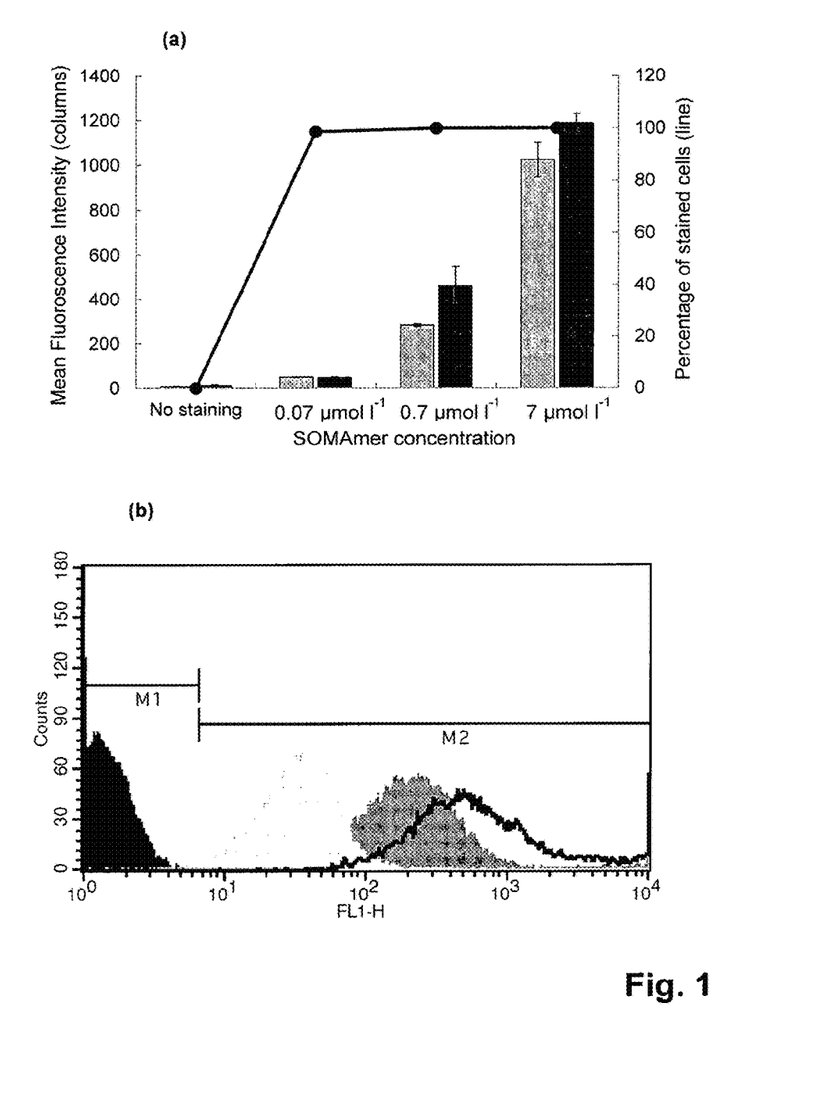
FIG. 1: Detection of *Staphylococcus aureus* by flow cytometry after staining of $10^7$ cells with different concentrations of fluorescence labeled 4520-8 (SEQ ID NO:3) and 4531-56 (SEQ ID NO:1) SpA SOMAmers (15 min binding reaction).

While 100% of the cells are already stained at a low SpA SOMAmers concentration of 0.07 µmol $l^{-1}$, the mean fluorescence intensities increase substantially at higher reagent concentrations of 0.7 µmol $l^{-1}$ and 7 µmol $l^{-1}$ (FIG. 1a). The data are consistent with the expected increase in saturation of highly abundant cell surface components with the fluorescence labeled SOMAmers. The minimal concentration of SpA SOMAmers to ensure a precise discrimination by flow cytometry between the negative populations (unstained cells) and the positive populations (stained cells) can be set up at 0.07 µmol $l^{-1}$ (FIG. 1b).

Figure 2:
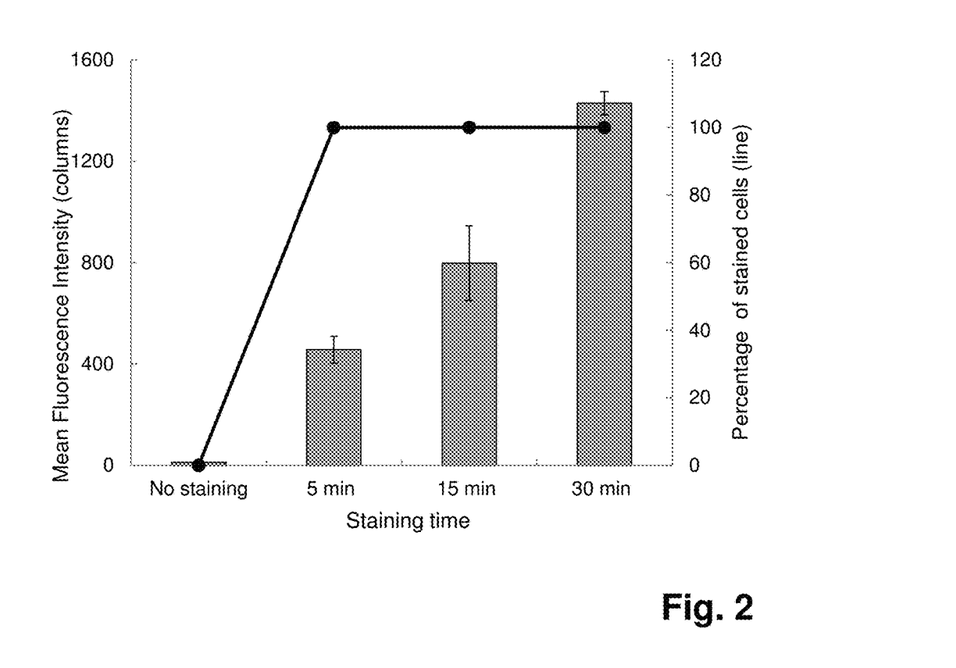
FIG. 2: Detection of *Staphylococcus aureus* by flow cytometry after staining of $10^7$ cells with fluorescence labeled 4531-56 (SEQ ID NO:1) SpA SOMAmers at 7 µmol l$^{-1}$. Comparison of different staining times (n=3). Mean fluorescence intensities are represented in columns and percentages of stained cells as line graph.
Figure 3:
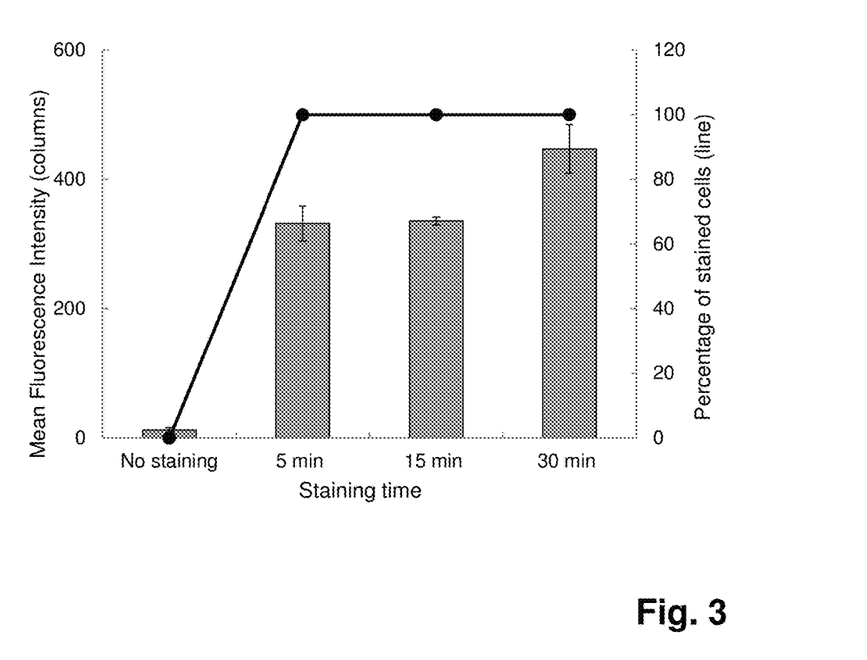
FIG. 3: Detection of *Staphylococcus aureus* by flow cytometry after staining of $10^7$ cells with fluorescence labeled 4531-56 (SEQ ID NO:1) SpA SOMAmers at 0.7 µM. Comparison of different staining times (n=3). With a 30-min staining incubation, the mean fluorescence intensity is improved by 1.4 times, compared to the intensity obtained after a 5-min staining incubation.

In order to define the optimal binding time, a time-course assay is performed. After only a 5-min binding reaction, 100% of the cells are already stained in the presence of 7 µmol $l^{-1}$ SpA SOMAmers (FIG. 2). By increasing the binding time to 15 and 30 minutes, the fluorescence intensities are improved about 2-fold and 3-fold, respectively, leading to a better discrimination between the negative population and the positive population. This increase in fluorescence intensity is less pronounced when the cells are labeled with a lower SpA SOMAmers concentration (0.7 µmol l$^{-1}$), likely due to limiting SOMAmers concentration (FIG. 3).

The SpA SOMAmers developed prove to have a high staining efficiency for *S. aureus*. In the experimental conditions, the optimal detection of *S. aureus* by flow cytometry is achieved in a simple one-step procedure using a low reagent concentration (0.7 µmol l$^{-1}$) and a short binding time (15 min). DNA aptamers have already been reported for the flow cytometry-based detection *of S. aureus* using single or combined aptamers (Cao et al. 2009) or for the detection of *Salmonella typhimurium* using aptamers generated by whole-cell SELEX (Dwivedi et al. 2013). However, the percentages of aptamer-labeled cells obtained in these studies did not approach 100% and the fluorescence intensities were weaker compared to the fluorescence intensities obtained with the SOMAmers of the present invention.

Example 5: Comparison of SOMAmers According to the Present Invention with Standard Aptamers Due to the unique slow off-rate feature of SOMAmers according to the present invention, these reagents should have a better affinity and better kinetic properties compared to standard RNA or DNA aptamers. In order to prove this statement, SpA SOMAmers according to the present invention are compared to DNA aptamers specific to *S. aureus* (unknown target antigen).

The DNA aptamers are manufactured by Integrated DNA Technologies.

The protocol for both the inventive aptamers and the standard aptamers is the same as the one described in Example 4 (exception for standard aptamers: no heating of the aptamers before the assay; PBS is used as the binding buffer).

Flow-cytometry results obtained with *S. aureus* DSM 1104:

| | Binders concentration | Binding time | Percentage of stained cells | Mean fluorescence intensity |
|---|---|---|---|---|
| SOMAmers (4531-56; (SEQ ID NO: 1)) | 0.7 µmol l$^{-1}$ | 5 min | 100% | 331 |
| Standard aptamers | 159 µmol l$^{-1}$ | 60 min | 90% | 265 |

The percentage of stained cells obtained with 159 µmol l$^{-1}$ of standard aptamers doesn't reach 100% after a 60-min binding time. Whereas with 0.7 µmol l$^{-1}$ of SOMAmers according to the present invention, 100% of cells are stained in only 5 minutes. This result demonstrates that the binding efficiency of the SOMAmers according to the present invention is better than standard DNA aptamers even with a 200 times lower concentration.

This experiment proves the benefit of the slow off-rate features of the SOMAmers according to the present invention for the flow cytometry detection of *S. aureus*: a higher binding/detection efficiency can be achieved with a lower reagents concentration in a very short time frame.

The invention claimed is:

1. A method of detecting a microorganism in a sample, comprising
   a) incubating the sample with a slow off-rate modified aptamer (SOMAmer) comprising a fluorescent label,
   b) optionally washing the sample,
   c) analyzing the sample by a fluorescence-based detection method,
wherein the SOMAmer comprises
   the nucleotide sequence of SEQ ID NO:1, or
   the nucleotide sequence which is fully complementary to SEQ ID NO:1,
wherein the microorganism is *Staphylococcus aureus*.

2. The method of claim 1, wherein the fluorescence-based detection method is a method selected from the group consisting of flow cytometry, solid-phase cytometry, fluorescence-based analytical methods, and fluorescence imaging system.

3. The method of claim 1, wherein the sample is a clinical sample, a food or feed sample, a beverage sample, a pharmaceutical sample, a personal care or cosmetic sample and/or a water sample.

4. The method of claim 1, wherein the SOMAmer comprises a nucleotide sequence specific for *Staphylococcus aureus*.

5. The method of claim 1, wherein the fluorescent label is selected from the group consisting of fluorescein dyes rhodamine dyes, cyanine dyes, Peridinin chlorophyll (PerCP), R-Phycoerythrin, coumarine dyes and quantum dots.

6. The method of claim 1, wherein the SOMAmer comprises the nucleotide sequence of SEQ ID NO:1.

* * * * *

SEQUENCE LISTING

```
<160> NUMBER OF SEQ ID NOS: 16

<210> SEQ ID NO 1
<211> LENGTH: 39
<212> TYPE: DNA
<213> ORGANISM: Artificial Sequence
<220> FEATURE:
<223> OTHER INFORMATION: SOMAmer: target SpA
<220> FEATURE:
<221> NAME/KEY: t
<222> LOCATION: (1)..(1)
<223> OTHER INFORMATION: C-5 modified pyrimidines

<400> SEQUENCE: 1
gctcgagtta attcgggatc gggctccggc ttttcgaat                          39

<210> SEQ ID NO 2
<211> LENGTH: 40
<212> TYPE: DNA
<213> ORGANISM: Artificial Sequence
<220> FEATURE:
<223> OTHER INFORMATION: SOMAmer: Target SpA
<220> FEATURE:
<221> NAME/KEY: t
<222> LOCATION: (1)..(1)
<223> OTHER INFORMATION: C-5 modified pyrimidines

<400> SEQUENCE: 2
ccggcttcgg gtacctatta tcggtttagc ccagtcataa                         40

<210> SEQ ID NO 3
<211> LENGTH: 40
```

```
<212> TYPE: DNA
<213> ORGANISM: Artificial Sequence
<220> FEATURE:
<223> OTHER INFORMATION: SOMAmer: Target SpA
<220> FEATURE:
<221> NAME/KEY: t
<222> LOCATION: (1)..(1)
<223> OTHER INFORMATION: C-5 modified pyrimidines

<400> SEQUENCE: 3
tcggcttcgg gtacctatta tcggtttagc ccagtcagaa            40

<210> SEQ ID NO 4
<211> LENGTH: 40
<212> TYPE: DNA
<213> ORGANISM: Artificial Sequence
<220> FEATURE:
<223> OTHER INFORMATION: SOMAmer: target SpA
<220> FEATURE:
<221> NAME/KEY: t
<222> LOCATION: (1)..(1)
<223> OTHER INFORMATION: C-5 modified pyrimidines

<400> SEQUENCE: 4
gcggcttcgg gtacctatta tcggtttagc ccagtcaaaa            40

<210> SEQ ID NO 5
<211> LENGTH: 40
<212> TYPE: DNA
<213> ORGANISM: Artificial Sequence
<220> FEATURE:
<223> OTHER INFORMATION: SOMAmer: target SpA
<220> FEATURE:
<221> NAME/KEY: t
<222> LOCATION: (1)..(1)
<223> OTHER INFORMATION: C-5 modified pyrimidines

<400> SEQUENCE: 5
gtggcttcgg gtacctatta tcggtttagc ccagtcagaa            40

<210> SEQ ID NO 6
<211> LENGTH: 40
<212> TYPE: DNA
<213> ORGANISM: Artificial Sequence
<220> FEATURE:
<223> OTHER INFORMATION: SOMAmer: target SpA
<220> FEATURE:
<221> NAME/KEY: t
<222> LOCATION: (1)..(1)
<223> OTHER INFORMATION: C-5 modified pyrimidines

<400> SEQUENCE: 6
gcggcttcgg gtacctatta tcggtttagc cctgtcagga            40

<210> SEQ ID NO 7
<211> LENGTH: 48
<212> TYPE: DNA
<213> ORGANISM: Artificial Sequence
<220> FEATURE:
<223> OTHER INFORMATION: SOMAmer: target: SpA
<220> FEATURE:
<221> NAME/KEY: t
<222> LOCATION: (1)..(1)
<223> OTHER INFORMATION: C-5 modified pyrimidines

<400> SEQUENCE: 7
gtgatcgagc ggcttcgggt acctattatt ggtttagccc agtcagaa   48

<210> SEQ ID NO 8
```

```
<211> LENGTH: 40
<212> TYPE: DNA
<213> ORGANISM: Artificial Sequence
<220> FEATURE:
<223> OTHER INFORMATION: SOMAmer: target SpA
<220> FEATURE:
<221> NAME/KEY: t
<222> LOCATION: (1)..(1)
<223> OTHER INFORMATION: C-5 modified pyrimidines

<400> SEQUENCE: 8
tcggcttcgg gtacctatta tcggtttagc ccagtctgaa                40

<210> SEQ ID NO 9
<211> LENGTH: 39
<212> TYPE: DNA
<213> ORGANISM: Artificial Sequence
<220> FEATURE:
<223> OTHER INFORMATION: SOMAmer: target SpA
<220> FEATURE:
<221> NAME/KEY: t
<222> LOCATION: (1)..(1)
<223> OTHER INFORMATION: C-5 modified pyrimidines

<400> SEQUENCE: 9
acggcttcgg gtacctatta tcggtttagc cagtcagaa                 39

<210> SEQ ID NO 10
<211> LENGTH: 40
<212> TYPE: DNA
<213> ORGANISM: Artificial Sequence
<220> FEATURE:
<223> OTHER INFORMATION: SOMAmer: target ClfA
<220> FEATURE:
<221> NAME/KEY: t
<222> LOCATION: (1)..(1)
<223> OTHER INFORMATION: C-5 modified pyrimidines

<400> SEQUENCE: 10
atctggttca aagtgacgat tgggcatctg gttttttaagt              40

<210> SEQ ID NO 11
<211> LENGTH: 40
<212> TYPE: DNA
<213> ORGANISM: Artificial Sequence
<220> FEATURE:
<223> OTHER INFORMATION: SOMAmer: target ClfA
<220> FEATURE:
<221> NAME/KEY: t
<222> LOCATION: (1)..(1)
<223> OTHER INFORMATION: C-5 modified pyrimidines

<400> SEQUENCE: 11
atctggttct aagttacttg gcgtaatctg gttttttaaga              40

<210> SEQ ID NO 12
<211> LENGTH: 40
<212> TYPE: DNA
<213> ORGANISM: Artificial Sequence
<220> FEATURE:
<223> OTHER INFORMATION: SOMAmer: target ClfA
<220> FEATURE:
<221> NAME/KEY: t
<222> LOCATION: (1)..(1)
<223> OTHER INFORMATION: C-5 modified pyrimidines

<400> SEQUENCE: 12
atctggttca aagtggcgat tgggcatctg gttttttaagt              40
```

```
<210> SEQ ID NO 13
<211> LENGTH: 25
<212> TYPE: DNA
<213> ORGANISM: Artificial Sequence
<220> FEATURE:
<223> OTHER INFORMATION: primer sequence clfA-3

<400> SEQUENCE: 13
cggatccagt agctgcagat gcacc                                                25

<210> SEQ ID NO 14
<211> LENGTH: 26
<212> TYPE: DNA
<213> ORGANISM: Artificial Sequence
<220> FEATURE:
<223> OTHER INFORMATION: primer sequence clfA-4

<400> SEQUENCE: 14
cgagctcgct catcaggttg ttcagg                                               26

<210> SEQ ID NO 15
<211> LENGTH: 34
<212> TYPE: DNA
<213> ORGANISM: artificial sequence
<220> FEATURE:
<223> OTHER INFORMATION: SOMAmer binding SpA
<220> FEATURE:
<221> NAME/KEY: n
<222> LOCATION: (1)..(1)
<223> OTHER INFORMATION: no nucleotide or any unmodified or modified
      nucleotide
<220> FEATURE:
<221> NAME/KEY: W
<222> LOCATION: (1)..(1)
<223> OTHER INFORMATION: C-5 modified pyrimidine
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 15
ggcwwcgggw accwawwawn ggwwwagccn ngwc                                      34

<210> SEQ ID NO 16
<211> LENGTH: 23
<212> TYPE: DNA
<213> ORGANISM: artificial sequence
<220> FEATURE:
<223> OTHER INFORMATION: SOMAmer binding to ClfA
<220> FEATURE:
<221> NAME/KEY: W
<222> LOCATION: (1)..(1)
<223> OTHER INFORMATION: C-5 modified pyrimidine
<220> FEATURE:
<221> NAME/KEY: n
<222> LOCATION: (1)..(1)
<223> OTHER INFORMATION: 1 to 30 unmodified or modified nucleotides
<220> FEATURE:
<221> NAME/KEY: misc_feature
<222> LOCATION: (9)..(9)
<223> OTHER INFORMATION: n is a, c, g, or t

<400> SEQUENCE: 16
awcwggwcna wcwggwwwww aag                                                  23
```